United States Patent [19]

Schall, Jr.

[11] 4,363,634
[45] Dec. 14, 1982

[54] GLASS SUPPORT COATED WITH SYNTHETIC POLYMER FOR BIOPROCESS

[75] Inventor: Roy F. Schall, Jr., Glendora, Calif.

[73] Assignee: Akzona Incorporated, Asheville, N.C.

[21] Appl. No.: 170,216

[22] Filed: Jul. 18, 1980

[51] Int. Cl.³ .................. G01N 33/50; G01N 33/54; G01N 33/78; G01N 33/58

[52] U.S. Cl. .................. 23/230 B; 23/915; 65/60.3; 204/195 B; 204/195 M; 204/195 P; 422/57; 424/1; 427/2; 435/7; 435/180; 435/181; 436/531; 436/512

[58] Field of Search .................. 422/57; 23/230 B; 424/12; 65/60 B; 204/195 B, 195 M, 195 P; 427/2

[56] References Cited

U.S. PATENT DOCUMENTS

| | | | |
|---|---|---|---|
| 3,036,492 | 5/1962 | Rao | 356/246 |
| 3,519,538 | 7/1970 | Messing et al. | 435/176 |
| 3,646,346 | 2/1972 | Catt | 422/57 |
| 3,770,380 | 11/1973 | Smith | 424/12 X |
| 3,867,517 | 2/1975 | Ling | 424/1 |
| 3,918,817 | 11/1975 | Posgate | 356/208 |
| 3,948,745 | 4/1976 | Guilbault | 204/195 B |
| 3,957,741 | 5/1976 | Rembaum et al. | 526/312 |
| 3,959,080 | 5/1976 | Orth et al. | 195/63 |
| 3,966,580 | 6/1976 | Janata | 204/195 B |
| 3,967,001 | 6/1976 | Almsula et al. | 427/78 |
| 3,970,518 | 7/1976 | Giaever | 23/230 B X |
| 4,024,235 | 5/1977 | Weetall et al. | 424/1 |
| 4,035,316 | 7/1970 | Yen et al. | 260/2.5 |
| 4,046,723 | 9/1977 | Dorman | 260/8 |
| 4,073,713 | 2/1978 | Newman | 204/195 B |
| 4,081,334 | 3/1978 | Suzuki | 204/195 B X |
| 4,092,408 | 5/1978 | Litt | 422/57 |
| 4,105,410 | 8/1978 | Gutcho | 422/57 |
| 4,120,945 | 10/1978 | Gutcho | 422/57 X |
| 4,138,383 | 2/1979 | Rembaum et al. | 260/29.7 |
| 4,169,138 | 9/1979 | Jonsson | 422/57 X |
| 4,197,287 | 4/1980 | Piasio et al. | 424/1 |
| 4,224,125 | 9/1980 | Nakamura | 204/195 P X |
| 4,224,365 | 9/1980 | Ali-Zaidi | 65/60 B |
| 4,240,889 | 12/1980 | Yoda | 204/195 B |
| 4,242,191 | 12/1980 | Schindler | 204/195 M |
| 4,245,064 | 1/1981 | Drobnik | 435/178 X |
| 4,267,270 | 5/1981 | Stout | 435/7 |
| 4,278,651 | 7/1981 | Hales | 422/57 X |

FOREIGN PATENT DOCUMENTS 2476125 8/1981 France.

OTHER PUBLICATIONS

Derwent Abstract of FR 247 6125; 70287 D/39, A96B04D16X16(A14).

*Primary Examiner*—Sidney Marantz
*Attorney, Agent, or Firm*—Robert H. Falk; Charles A. Wendel; Francis W. Young

[57] ABSTRACT

A new and useful process is disclosed for manufacturing a device for use in a bioprocess, comprising: (a) providing solid support means insoluble in water or organic solvent solutions; (b) coating said solid support means with water-based polymeric film means capable of applying one or more biomaterials; and (c) adsorbing or covalently bonding at least one functional biomaterial to said polymeric film means. The polymeric film means, for example, can be used to coat antigens, antibodies, haptens, enzymes, living bacteria, yeasts, etc. (i.e., biomaterials) to a glass (or other) support material, e.g., a glass tube, with surprising retention of the biomaterial's essential characteristic properties. The solid support means include but are not limited to those comprising glass, ceramics, metals, polymers and woods. The device of the invention is particularly useful in various immunoassays using a solid support for separation of phases.

15 Claims, 4 Drawing Figures

THYROXINE-ENZYME ACTIVITY ON ANTI-THYROXINE AS A FUNCTION OF COATING PRECURSOR SUSPENSION CONCENTRATION

EIA REAGENTS ADAPTED TO POLYMER-COATED GLASS TUBES. STANDARDS RUN IN QUADRUPLICATE; CONTROLS AND RECOVERY SAMPLES RUN IN HEXAREPLICATE.

NORMAL RABBIT SERUM (ALL WELLS OF ROW)
1:10⁵ DILUTION RABBIT ANTI-hCG (")
1:10⁴ DILUTION RABBIT ANTI-hCG (")
1:10³ DILUTION RABBIT ANTI-hCG (")
1:100 DILUTION RABBIT ANTI-hCG (")

COORS PLATE COATING SCHEME

COLOR CODE: 0 = BLANK - NO COLOR, MINIMAL COLOR
5 = MAXIMUM COLOR
1,2,3,4 GRADATIONS OF COLOR LIGHTEST TO DARKEST

PATTERN OF COLOR FORMATION ON COORS PLATE

GLASS SUPPORT COATED WITH SYNTHETIC POLYMER FOR BIOPROCESS

RELATED APPLICATIONS

This invention is related to an application filed on even date by Roy F. Schall, Jr. and Stephen J. Lewis, Ser. No. 170,304, filed July 18, 1980, entitled "PROCESS OF APPLYING AN ADHESIVE ORGANIC-SOLVENT BASED POLYMERIC FILM TO INSOLUBLE SOLID SUPPORTS AND ATTACHING BIOMATERIALS THERETO".

BACKGROUND OF THE INVENTION

1. Field of the Invention

This invention relates to the field of biochemistry and to the sub-field of the manufacture of organic solvent-and/or water-insoluble solid supports, and specifically the manufacture of those supports coated with biologically, biochemically or immunochemically active materials (herein referred to henceforth as biomaterials) with retention of one or more of their desired characteristic biological, biochemical or immunochemical functionalities.

2. Description of the Prior Art

Many processes utilize biologically, biochemically, or immunochemically active ingredients attached to insoluble supports. In using such supports, essential steps in many processes may be expedited, may be simplified, may be made less expensive, or improved in other ways. Immobilized biomaterials already appear in literature. Excellent reviews are offered, among others, by R. B. Dunlap, editor, *Immobilized Biochemicals and Affinity Chromatography* (Plenum Press, New York, N.Y., 1974), and by H. H. Weetall, editor, *Immobilized Enzymes, Antigens, Antibodies, and Peptides—Preparation and Characterization* (Marcel Dekker, New York, N.Y., 1975). An especially comprehensive review of patented art is found in J. C. Johnson, editor, *IMMOBILIZED ENZYMES Preparation and Engineering, Recent Advances,* (Noyes Data Corporation, Park Ridge, N.J., 1979).

Messing et al. in U.S. Pat. No. 3,519,538 and Weetall and Yaverbaum in U.S. Pat. No. 4,024,235 each describe a method for bonding biomaterials directly to glass or ceramic supports by incorporating derivatives of silane compounds onto the silicaceous surfaces of a support and chemically coupling biologically or biochemically active molecules through the derivative linkages. The processes described in these patents, however, do not apply to nonsilicaceous materials such as metals, plastics, wood, etc.

Weetall teaches in U.S. Pat. No. 3,652,761 one method whereby organic, biological, or immunological materials can be bonded to glass. It involves the use of an organic silane linker to glass directly, and Weetall demonstrates improved stability of biological materials in this way. Weetall cites as disadvantages of the use of polymers (plastics) a non-specific adsorption and elution, poor flow rates (when used in columns), poor protein coupling efficiency and decreased biological activity. He requires covalent coupling to his glass support. In addition, Weetall shows no applicability to some materials (i.e., metals, nylon, etc.) other than glass.

Glass supports are especially useful in the immunoassay field where antigens and antibodies, respectively, can be bonded to glass media for use in separation steps. Glass is especially desirable as a support medium because of its optical and mechanical properties. In particular, glass tubes (which provide a water-insoluble, water-insuspensible support) bonded to antigens or antibodies are useful because of their relatively low cost and adaptability as cuvettes directly to colorimeters and nephelometers commonly available on the market. A good example of an advanced enzyme immunoassay using such tubes is U.S. Pat. No. 4,016,043 by Schuurs et al. See the teaching of U.S. Pat. Nos. 3,918,817, 3,967,001 and 3,036,492, and the BRICE-PHOENIX Model OM-2000 Light Scattering Photometer (Virtis Co., Gardner, N.Y.) and in particular Ser. No. 932,594, filed Aug. 9, 1978, now U.S. Pat. No. 4,213,764 incorporated herein.

However, glass supports have not always found universal use because of their limited capacity to bond or adsorb biomaterials. The problem is especially acute with respect to certain antigens and antibodies. For example, standard size immunoassay tubes (e.g., 10 mm×75 mm, 12 mm×75 mm, 13 mm×100 mm of glass and coated with thyroxine antibodies take up insufficient antibody to permit an assay in the range desired for most routine analytical testing. There are no commercially available antibody-coated glass tubes on the market now for immunoassays. Commercial clinical immunoassays using other kinds of glass supports are currently sold only by Corning Medical Co., Medfield, Mass., and by Electro-Nucleonics, Inc., of Fairfield, N.J., both of whom purvey assays in which fine glass particles are the supports.

In 1966, K. Catt, H. D. Niall and G. W. Tregar reported in *Biochem. J.* 100, 31C et seq. (1966) a method for applying serum and immunoglobulins to polymeric supports such that their biochemical functionalities remained essentially intact. Their supports included polystyrene, p-aminobenzylcellulose, and a graft copolymer of polystyrene and polytetrafluoroethylene. Many other workers have since described other polymeric supports with similar properties. See, for example, the work of Ling (U.S. Pat. No. 3,867,517); Tu (U.S. Pat. No. 4,166,844); R. Piasio et al., (U.S. Pat. No. 4,197,287); L. Wide and J. Porath, *Biochim. Biophys. Acta* 130 at 257 eq seq. (1966); S. A. Tillson et al., in *Immunologic Methods in Steroid Determination* (F. G. Peron and B. V. Caldwell, editors, Appleton-Century-Crofts, New York, N.Y., 1970); and many papers in *Immobilized Biochemicals and Affinity Chromatography,* R. B. Dunlap, editor (Plenum Press, New York, N.Y., 1974); and in *Immobilized Enzymes, Antigens, Antibodies, and Peptides—Preparation and Characterization,* H. H. Weetall, editor (Marcell Dekker, Inc., New York, N.Y. 1975). Again the supports usable with these techniques were limited to polymeric materials.

Catt teaches in U.S. Pat. No. 3,646,346 the use of solid plastic tubes to perform radioimmunoassays. Catt apparently made no attempt to coat glass, and in Catt's teaching, only adsorption of protein was possible.

Bennich et al. in U.S. Pat. No. 3,720,760 taught attaching immunologically active molecules to insoluble polysaccharide (polymeric) beads of the type sold under the trademark SEPHADEX ™. Such beads are unstable to swelling upon hydration, their interstices are inherently difficult to wash or rinse, and they have poor mechanical stability (may be crushed, compacted, etc.).

E. A. Fischer has taught by way of U.S. Pat. No. 4,181,636 use of suspensions of polymeric beads for purposes similar to that of Bennich. Neither Bennich nor Fischer described applying the particles to nonsuspendable solid surfaces, which would render them useful without centrifugation. The processes they describe also were limited to the use of polymeric materials.

The substitution of polymeric for nonpolymeric materials will, in many instances, increase the capacity of a solid support to adsorb biomaterials. While, for example, glass will adsorb biomaterials that remain functional, glass supports have not proven as popular in commercial and laboratory applications as have polymeric supports, partly (as indicated above) because their capacity to take up biomaterials is typically less than that of similar surfaces molded from polymeric materials. Many manufacturers offer products similar to glass supports comprising polymers. Mallinckrodt Inc., St. Louis, Mo.; Clinical Assays (Division of Travenol Laboratories, Inc.), Cambridge, Mass.; Squibb, Inc., Princeton, N.J.; Organon Diagnostics, West Orange, N.J.; Abbott Laboratories, Inc., Chicago, Ill.; Cordis Corp., Miami, Fla.; Becton-Dickenson, Inc., Orangeburg, N.Y.; North American Biologicals, Inc., Miami, Fla.; Bio-Rad Laboratories, Richmond, Calif.; RIA Products, Waltham, Mass.; M.A. Bioproducts, Walkersville, Md.; Worthington Diagnostics (Division of Millipore Inc.), Freehold, N.J.; Millipore Inc., Bedford, Mass.; Dade Reagents Inc., Miami, Fla.; Wellcome Reagents, Research Triangle Park, N.C.; Micromedic Systems, Inc.; Horsham, Pa.; Ramco Inc., Dallas, Tex.; Ventrex Inc., Portland, Maine; Litton Bionetics, Kensington, Md.; and New England Immunology Associates, Cambridge, Mass.

Unfortunately, plastic supports have inferior thermal stability vis-a-vis glass—they are amenable to warping by heat and can therefore be deformed. They do not have the desired optical properties of glass. In particular, for fluoresence and enzyme immunoassays, most plastic tubes are very inappropriate because they are opaque or translucent, and/or have optically irregular and inferior surfaces. Because of the increasing price of petrochemicals, their cost is always uncertain. More importantly, supports made of opaque or translucent polymers or polymers with irregular and inferior surfaces cannot be adapted as self-contained cuvettes. In many instances, immunoassays using these supports contain solutions which must be transferred to a glass cuvette. Plastic tubes almost invariably cannot be used with common spectrophotometers.

Hence, an acute need arose in the biochemical field, (particularly the immunoassay art) for a surface to take up biomaterials (e.g., antibodies, antigens, or haptens) which have the adsorptive properties of plastic, but have the same optical and mechanical properties as glass.

It is also known in the art to coat metals with biomaterials. For example, see M. Charles et al. in *Immobilized Biochemicals and Affinity Chromatography*, R. B. Dunlap, editor (Plenum Press, New York, N.Y., 1974), at 213 et seq. and N. Yamamoto et al., *Chemistry Letters (Japan)* at 245-246 (1978), who describe methods for applying biomaterials with functional retention of their essential properties to stainless steel, titanium and other dense metals. Methods taught by these authors, however, are by their teachings limited to the materials described, and are not taught to be widely applicable to other support materials like polymers or wood.

S.-P. S. Yen, A. Rembaum and R. S. Molday described in U.S. Pat. No. 4,206,094 a way of preparing extremely small, magentically responsive, polymer-coated particles possessing functional biomaterials. Their process and invention was limited only to metals, metal compounds of electron-dense metals having an atomic number greater than 50 or magnetically attractive metals. The particles were formed in situ by copolymerization of monomers and metal particles. Applicability to macrosupports and to materials other than metals was not shown. Furthermore, the formation of their materials from organic solvents was not demonstrated.

Recently, R. A. Harte described in U.S. Pat. No. 4,133,639 a vessel and handle device prepared from glass or plastic which was useful as a reaction vessel for quantitation of materials in biological solutions. The teaching of Harte requires covalent bonding of active reagents to the walls of the vessel and requires stirring through use of the handle.

DISTANT ARTS

Several patents in distant arts, unavailable as prior art to the instant invention, became known to us after the date of our invention described herein; these disclose processes for preparing and applying polymeric films to glass surfaces. J. E. Thomson and G. E. Waples (U.S. Pat. No. 3,520,861), G. W. Prejean (U.S. Pat. No. 4,056,208), J. C. Gebhard, Jr. et al. (U.S. Pat. No. 4,056,653) and G. A. Salensky (U.S. Pat. No. 4,065,590) all disclose processes for making and coating glass with a polymeric film. None, however, demonstrates the application of biomaterials to the polymeric coating of the glass or other solid support materials. Each process was designed to alter the strength, resistance to chemical attack, or safety of glass vessels and bottles. Thomson and Waples disclosed improved formulations for plastic copolymers. The specific goals were improved tenacity of the coating material to glass, improved printability on the polymeric surface, and a tightly adherent surface for other coating materials as between laminate layers. They did not mention nor contemplate putting biomaterials on the layers.

Prejean applied two layers to glass: (1) epoxy resins and an organo-functional silane in either a mixed layer or separate layers (a primer layer) followed by (2) a copolymer of an alpha-olefin. These layers imparted an improved surface to a glass vessel against attack by alkali. The Prejean process required toxic (mutagenic) epoxides, applying two layers and merely resulted in a surface protected from caustic solutions. Again, no attempt was made to apply biological materials to the coating, nor was any suggestion offered that this was feasible.

In U.S. Pat. No. 4,056,653, Gebhard, Waggoner, and Webster teach the manufacture of a free-flowing powder useful for preparing clear, protective, shatter-resistant coatings for glass and protective coatings for metals and other materials. The Gebhard et al. teaching relates to the generation of raw materials to achieve these coatings. Once again, no effort was made, nor suggestion expended, to use these coatings for biological, biochemical, or immunochemical purposes.

Salkensky taught in U.S. Pat. No. 4,065,590 a shatter-resistant bottle covering for single trip consumer use. No application to biological systems was contemplated or suggested.

Bruschi teaches in U.S. Pat. No. 4,066,403 a multiple layer arrangement of reactants on a support in which a barrier layer plays a critical role in diffusion of some reagents/products but not others. The invention describes self-contained test reagents for a variety of analytes in body fluids, but it is not intended for systems as complex as immunoassays. In addition, contact with water based fluids probably results in swelling of the Brushi reagents.

Not only is there a lack of any teaching of the use of these coating methods to bind a biomaterial to a water-insoluble surface such as glass (or porcelain, metal or wood), there is no mention of applying these coatings in such effective thicknesses to retain the optical properties of glass while at the same time avoiding chipping or peeling of the polymeric layer.

SUMMARY OF THE INVENTION

I have found that by coating traditional rigid supports with polymeric films, often the best properties of each material are combined advantageously and inexpensively. For example, ceramic rods coated with polymeric film possess the excellent adsorptive properties of the polymer, but are very resistant to physical deformation or heat that might flex or warp a plastic rod. I have also found that solid supports with a polymeric coating surprisingly bond biological, biochemical and immunochemical materials (i.e., "biomaterials") with a surprising level of retention of one or more of the desired biochemical properties, i.e., the biomaterials retained are "functional". In particular, coating glass support means with a water-based polymeric film has surprisingly been found to increase dramatically the capacity of the glass support to adsorb the biomaterials and thereby improve the effectiveness in utility of the bare glass support.

The present invention thus concerns, inter alia, the application of adhesive films of water-based polymers to many insoluble support materials for the purposes of adsorbing or covalently bonding biomaterials to these supports such that their biofunctionality remains substantially unimpaired. The present invention includes the use of such coated supports in diverse scientific, industrial and clinical applications involving biological, biochemical and immunochemical processes, i.e., bioprocesses. Examples of bioprocesses include, but are not limited to, immunoassays, competitive binding assays, enzyme determinations, brewing, catalytic processes, etc.

One embodiment of the process of my invention first comprises a step of applying a solution or suspension of water-based polymeric material to solid surfaces such that a film coating forms. Drying and curing the film then takes place to make it water-insoluble, tightly adhesive and stable. The film at this stage is adsorptive to biomaterials. Further, after heat curing, some polymeric films used in the process of our invention possess free carboxylate groups or other chemically active groups to which reactive chemical groups on the biomaterials may be covalently coupled by known chemical principles, i.e., these biomaterials may be covalently bonded to the film such that their essential functionalities are substantially retained intact on the film. Other biomaterials employed simply adsorb to the polymeric film, and still retain their effective functionalities.

As stated above, the film or layer formed by the process of my invention is capable of adsorbing or covalently bonding biologically active, biochemically active or immunochemically active substances with retention of their biological, biochemical, or immunochemical properties. Films may be formed from water-based polymeric or copolymeric suspensions, as desired by the user, and may not require organic solvents, extraordinary equipment, or complicated processes. With alternative starting materials, nonaqueous solvents may be used. By varying the concentration of coating fluid initially used, the thickness of the film formed can be varied from very thin (less than one micrometer and invisible) to very thick (visible).

More specifically, the device of the invention is to be employed in a predetermined biological, biochemical or immunochemical process (i.e., a "bioprocess"). In its broadest application, the novel device of the invention comprises:

(a) solid support means insoluble in a solvent selected from the group consisting of water and organic solvent solutions, which solid support means is coated with water-based polymeric film means capable of adsorbing or covalently bonding one or more functional biomaterials; and (b) one or more functional biomaterials adsorbed or covalently bonded to said polymeric films.

Of course, the method of using said novel device in a bioprocess is also part of the invention.

Correspondingly, in its broadest application, the process of the invention for manufacture of the novel device comprises:

(a) providing a solid support means insoluble in water or organic solvent solutions;

(b) coating said solid support means with polymeric film means capable of adsorbing or covalently bonding one or more functional biomaterials; and (c) adsorbing or covalently bonding at least one functional biomaterial to said polymeric film means.

Preferably, the solid support means is water-insoluble, water-insuspensible, and, most preferably, comprises a glass tube. If the bioprocess is an immunoassay, the functional biomaterial is generally selected from the group consisting of an antigen, an antibody, or a hapten.

A much preferred process for the manufacture of the novel device comprises:

(a) providing solid support means insoluble in water or organic solvent solutions;

(b) heating the solid support from about 20° C. to about 100° C.;

(c) heating a water-based, film-forming polymeric suspension from about 20° C. to about 100° C.;

(d) coating said heated solid support means with said heated polymeric suspension;

(e) drying the coated solid support means to remove any water and to form a polymeric film on said solid support means, which film is capable of adsorbing or covalently bonding one or more functional biomaterials;

(f) heating the solid support means having said film from about 100° C. to about 200° C. for a time sufficient to cure said film;

(g) cooling the solid support means having said cured film to a temperature suitable for applying one or more functional biomaterials to said cured film; and (h) adsorbing or covalently bonding at least one functional biomaterial to said polymeric film means.

Preferably, heating step (f) above is conducted from about 1 minute to about 2 hours; preferably, the temperature to which the support means with cured film is cooled is about room temperature.

DESCRIPTION OF THE PREFERRED EMBODIMENTS

Figure 1:
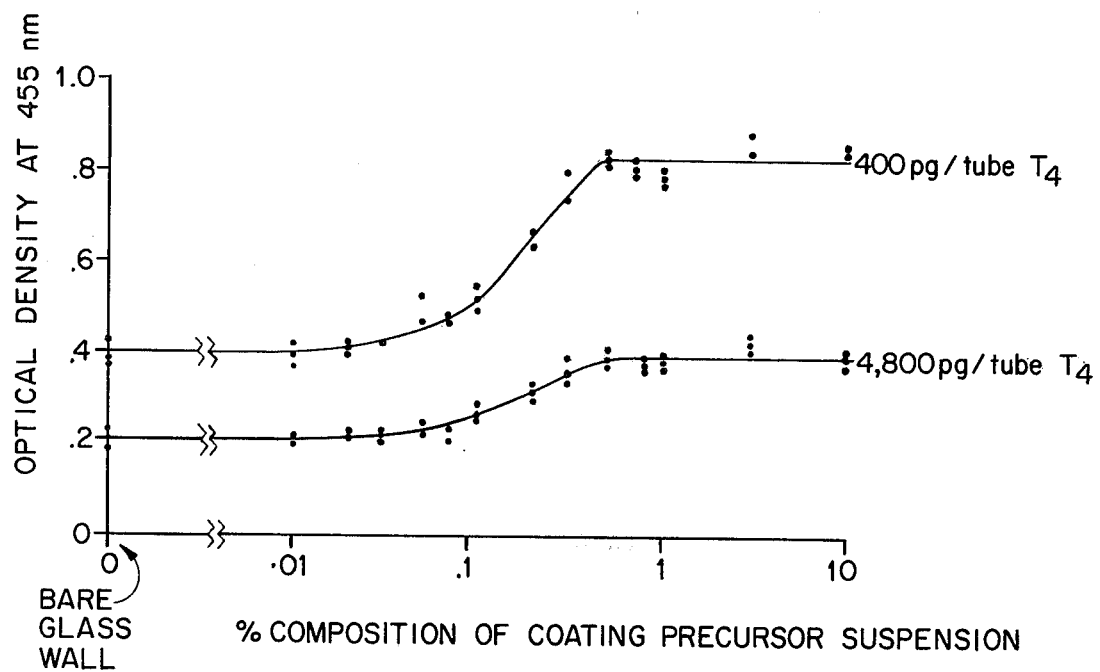
FIG. 1 is a semilogarithmic plot of Absorbances of Thyroxine($T_4$)-Enzyme Activity read spectrophotometrically at 455 nm (ordinate) versus the concentration of Coating Precursor Suspension Concentration (abscissa), resulting from experiments run forming the basis of Example 1.

The present invention includes a novel and useful process, wherein a polymeric film is applied from a solution or suspension to solid support means such that after drying and curing, a toughly adherent, stable film coats the support means. Afterwards, one or more biomaterials are adsorbed or covalently bonded to this film.

The film which is formed may be used for bonding biologically active, biochemically active or immunochemically active substances, i.e., biomaterials. The film is inherently adsorptive of such biomaterials, and biomaterials may be applied by adsorption to the film with quite satisfactory results. The film can be applied so as to cause no or minimal distortion to a beam of light (i.e., the film will be flat and smooth). Hence, uncoated tubes and the novel polymeric film-coated glass tubes of our invention as cuvettes can be used equally as well by spectrophotometers.

Many suitable starting polymeric materials possess chemically reactive groups to which biomaterials may be covalently bonded by known chemical means. Thus, solid support means insoluble in water (or, in the alternative, an organic solvent may be used see application Ser. No. 170,304) may be comprised of glass, ceramics, metals, plastics, wood, etc., or any solid support material capable of being coated by the (suitable) polymeric film means. Thus, different practical shapes—spheres, tubes, etc.—may be coated with a polymeric surface suitable for bonding to predetermined biomaterials by chemical or adsorptive means. The coated materials may then be applied in diverse useful applications including the chemical, biochemical, and medical fields.

One preferable starting material is an anionic, translucent hydrosol of a 300 melt index ethylene-acrylic acid (about 80% ethylene, about 20% acrylic acid) copolymer, 100% neutralized with $NH_4OH$ and containing no additional surfactants or stabilizers. The solids content of the starting material is approximately 19% to 26%. It is marketed by Dow Chemical U.S.A. (Midland, Mich.) as XD-8931 aqueous olefin dispersion or as XD-60899 aqueous olefin dispersion.

Similar polymeric film means leading to coated surfaces with similar properties and potential uses are manufactured and sold by others. Table 1 lists some additional representative suitable polymeric film means and their suppliers.

TABLE 1
ADDITIONAL FILM FORMING POLYMERIC MATERIALS AND THEIR SUPPLIERS

| TRADE NAME | MAKER | SOLVENT OR SUSPENDING MEDIUM | POLYMER COMPOSITION |
|---|---|---|---|
| CARBOSET ® Acrylic Resins: XL-11, XL-19, 514 H, 531 | B. F. Goodrich Chemical Co., 6100 Oak Tree Blvd., Cleveland, Ohio | Ammonia—$H_2O$ | Copolymers of acrylic acid and acrylate esters; otherwise not specified. |
| CARBOSET ®: 514A | B. F. Goodrich Chemical Co., 6100 Oak Tree Blvd., Cleveland, Ohio | Iso-propanol | Copolymers of acrylic acid and acrylate esters; otherwise not specified. |
| CARBOSET ®: 515 | B. F. Goodrich Chemical Co., 6100 Oak Tree Blvd., Cleveland, Ohio | 100% Liquid Resin | |
| GELVA ®: TS-23, TS-30, TS-65, TS-85, S-51, S-52, S-55R, S-77, S-97, S-98 | Monsanto Co., 800 North Lindbergh Blvd., St. Louis, Mo. | $H_2O$ | Polyvinylacetate, otherwise not specified. |
| GELVA ®: C-3, TS-70, TS-71, TS-100, 900, 925 | Monsanto Co., 800 North Lindbergh Blvd., St. Louis, Mo. | $H_2O$ | Polyvinyl acetate copolymer or multipolymer; otherwise not specified. |
| ACRYLOID ®: A-10, A-11, A-101, A-21, A-21LV, A-30, B-44, B-48N, B-50, B-66, B-67, B-67MT, B-72 | Rohm & Haas Co., Independence Mall West, Philadelphia, Pa. 19105 | Various organic solvents | Various methacrylate polymers and copolymers; otherwise not specified. |
| ACRYLOID ® B-52, B-84, B-99, C10LV, F-10, NAD-10 | Rohm & Haas Co., Independence Mall West, Philadelphia, | Various organic solvents | Various methacrylate polymers and copolymers; otherwise not specified. |

TABLE 1-continued

ADDITIONAL FILM FORMING POLYMERIC
MATERIALS AND THEIR SUPPLIERS

| TRADE NAME | MAKER | SOLVENT OR SUSPENDING MEDIUM | POLYMER COMPOSITION |
|---|---|---|---|
| | Pa. 19105 | | |

Any polymeric material is suitable for a polymeric film as long as it is capable of coating the solid support means, is water-based (or organic-solvent-based as desired—see application Ser. No. 170,304), can be cured, and is capable of adsorbing or covalently bonding one or more functional biomaterials.

In a preferred application, the Dow Chemical Co. hydrosol starting material above is diluted to a useful dilution (approximately 1% to 10% solids) with 1% $NH_4OH \cdot H_2O$. See Example 1. The item to be coated and the dilution of copolymer hydrosol are usually warmed to a temperature in excess of about 30° C., most preferably about 50° C., and the object to be coated immersed in the hydrosol dilution. The coated object is removed and permitted to drain and air dry. At this point, a film has formed, but the film is easily destroyed by rewetting the surface of the object with water. After the object is dry, it is heated at a temperature in excess of about 100° C., but less than 200° C., most preferably about 140° C., for a time sufficient to cure the film, preferably for ½ hour. In the curing process, $NH_3$ is driven off, causing the copolymer salts to revert to free carboxylic acid. In addition, the film becomes tightly adherent and adsorbent of biomaterials. After curing, it is also impervious to water. The object is cooled to ambient temperature. The coated object is now ready for application of biomaterial, either by adsorption, or by covalent coupling by chemical means known to those in the art.

Although the invention has been described with reference to specific embodiments above, numerous variations and modifications will become evident to those skilled in the art, without departing from the scope and spirit of the invention as described above, defined in the appended claims, and as shown in the following Examples I-VI:

EXAMPLE 1

Coating of a Glass Surface With Polymer and Subsequently With Antibody by Adsorption A 24.4% by weight hydrosol dispersion of Dow Chemical U.S.A. (Midland, Mich.) ethylene-acrylic acid copolymer preparation XD-8931 (Lot No. AD 0906914.1, pH 9.6) was diluted in a series from 0.01% to 10% by weight solids with 1% $NH_4OH-H_2O$ solution. The Dow preparation is currently used as a burst-preventing film coating for carbonated soft drink bottles and as weather proofing for outdoor advertising. Glass tubes (13×100 mm) in triplicate and at ambient temperature were filled with the dilutions of coating hydrosol such that a series of tubes with films formed from each dilution would be prepared. The tubes were emptied by decantation, inverted over adsorbent paper, drained and permitted to air dry. After the tubes were air dried, they were heated to about 110° C. for about 15 minutes in an oven, removed and permitted to cool to room temperature (about 25° C.), leaving a smooth, tough, tightly adhering film on glass which remained water-insoluble. The film contained carboxylate groups to enable easy covalent chemical attachment of biomaterials by known accepted chemical materials. The film was non-toxic, and because it is water-based did not require the use of poisonous or flammable organic solvents.

The globulin fraction of serum from rabbits hyperimmunized against thyroxine-bovine serum albumin (BSA) was obtained by salt fractionation and chromatography on ion exchange gels by standard methods. The purified globulin was diluted to 10 μg/ml with 0.0175 M phosphate at pH 7.6. About nine (9) ml of the solution was incubated in each tube overnight at room temperature. The tubes were then washed three times with phosphate buffer. A set of uncoated glass tubes was treated in the same way as were the polymer-film coated tubes.

Into each tube was placed a thyroxine-horseradish peroxidase conjugate prepared as described in *Clin. Chem.* 24 at 1803 et seq. (1978), and 1.0 ml of phosphate buffer containing 0.2% BSA, pH 7.6 and unconjugated thyroxine (400 pg/tube or 4,800 pg/tube). The contents of the tubes were incubated for one hour at 37° C. and decanted. The tubes were rinsed twice with 3 ml each of a solution containing 0.01% TRITON® (Rohm and Haas, supra) N-101 (surfactant) wetting agent in $H_2O$. Enzyme activity was subsequently determined by adding to each tube 2 ml of a solution of 0.033 M citric acid and 0.067 M phosphate ion, pH 5.0, containing per tube 0.88 mg urea peroxide substrate and 1.4 mg o-phenylenediamine dihydrochloride chromogen. After about 20 minutes, 1 ml of 1 M citric acid and 0.1% $NaN_3$ were added to stop and fix the color reaction. Absorbances were read in each tube spectrophotometrically at 455 nm wavelength.

The absorbances were then plotted on semilogarithmic paper (ordinate) against the solids concentration of the coating suspension (abscissa). FIG. 1 shows that coated tubes not only took up functional antibody, but that they took up surprisingly more functional antibody when polymer-coated than bare glass tubes, and the enzyme activity associated with coated tubes was much higher than bare glass tubes. Furthermore FIG. 1 shows that within limits, the amount of biomaterials adsorbed to the surfaces of the tubes can be controlled by the concentration of coating precursor suspension used.

EXAMPLE 2

Coated Glass Tubes and Adsorbed Antibody; Use as Self-Contained Reaction Vessels and Cuvettes for Enzyme Immunoassay A second, larger batch of tubes than Example 1 was prepared from a 1% polymer suspension warmed to about 57° C. The tubes were warmed to about 60° C. and then filled with the coating suspension as in Example 1. The filled tubes were then warmed further to about 90° C. They were decanted, air-dried and cured for one hour at 141° C. Antibody was adsorbed to them in the manner described and taught in Example 1.

The tubes were then used in a competitive enzyme immunoassay for thyroxine ($T_4$). See U.S. Pat. No.

3,654,090, incorporated herein. The tubes were used as both reaction vessels and as cuvettes for and spectrophotometric readout of results. Pipetted into the tubes were 20 μl of the appropriate serum calibrator, control, dilution of serum or thyroxine-spiked serum, 100 μl of thyroxine-horseradish preoxidase conjugate (as label) containing 1,000 μg/milliliter of 8-anilino-1-naphthalene sulfonic acid, and 900 μl of 0.1 M of phosphate buffer containing 0.2% BSA, pH 7.6. All tubes were mixed thoroughly, incubated for about one hour at 37° C., and decanted. Each tube was washed twice with 3 ml TRITON ® N-101 wetting agent and color developed as in Example 1 above. The absorbances of all tubes were then read by a Spectronic 20 spectrophotometer (Bausch & Lomb, Rochester, N.Y.) capable of accepting 13 mm×100 mm round tubes.

Figure 2:
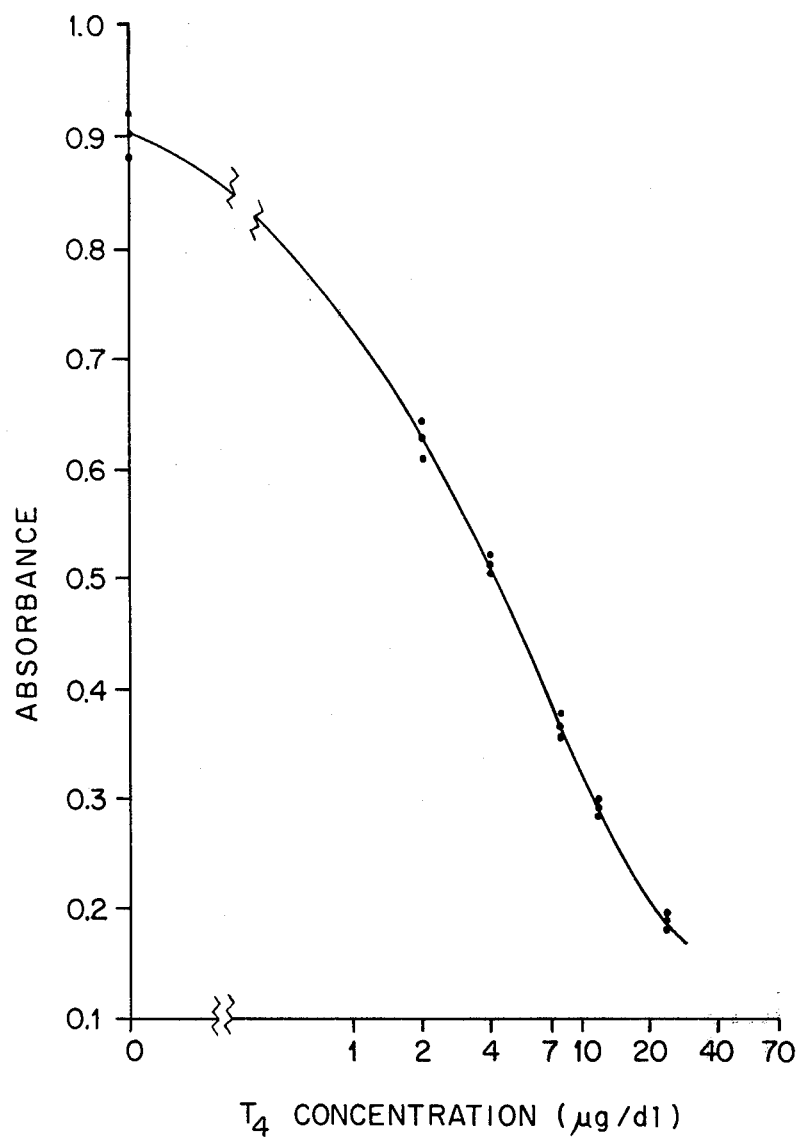
FIG. 2 is a semilogarithmic plot of thyroxine ($T_4$) concentration (abscissa) versus absorbance at 455 nm read by a spectrophotometer (ordinate), resulting from experiments run forming the basis of Example 2.

FIG. 2 and Table 2 present a standard curve and recovery results for the assay using the tubes as self-contained reaction vessels and cuvettes.

TABLE 2

| RECOVERY RESULTS, EXAMPLE 2 | | | | |
|---|---|---|---|---|
| (1) | $\Delta T_{0-24}$ = 52.2% | | | |
|  | $\Delta T_{2-24}$ = 41.9% | | | |
| (2) | Sample | Value (μg/dl) | Recovery | % CV |
|  | C1 | 3.2 ± .3 | 91% | 9.4 |
|  | C2 | 12.7 ± .7 | 94% | 9.5 |
| (3) | Recovery | | | |
|  | 1 | 5.8 ± .7 | 96% | 12.1 |
|  | 2 | 8.3 ± .4 | 98% | 4.8 |
|  | 3 | 10.3 ± .7 | 94% | 6.8 |
|  | 4 | 13.5 ± 1.1 | 100% | 8.2 |
|  |  | Average | 97 ± 3% | 8.0 ± 3.1% |

EXAMPLE 3

Coating a Glass Surface and Attaching Antibody by Covalent Bonding

A film of copolymer was applied from 1% suspension of the Dow XD-8931 polymer above in $H_2O$-$NH_4OH$ as outlined and taught in Example 1, dried, and cured at 120° C. for 16 minutes. The tubes were then treated with a water solution of 0.438 g/l 1-cyclohexyl-3(2-morpholinoethyl)-carbodiimide metho-p-toluenesulfonate for four hours and rinsed with water. Antithyroxine rabbit IgG was diluted to 15 μg/ml and an aliquot of radiolabeled (Iodine-125) rabbit IgG was mixed with it. The solution was introduced into the film-coated tubes and incubated overnight at room temperature. In the morning, the tubes were decanted, rinsed with a solution containing 0.5% gelatin, 0.0175 M phosphate, pH 7.6, and 0.9% saline. The tubes were counted in a gamma counter to measure the amount of IgG bound to the surface. The tubes were then subjected to testing for functional antibody as described and taught in Example 1. Following the testing, the tubes were decanted and counted again, and the amount of radioactivity lost computed. As controls, tubes were treated like the covalently coupled tubes except that they were never exposed to carbodiimide. Table 3 summarizes the results for loss of protein and functionality of anti-thyroxine with these tubes.

The tubes containing covalently bound IgG showed improved stability to protein loss and improved loading of specific antibody compared to tubes with adsorbed antibody. Both kinds of tubes were quite functional.

TABLE 3

COMPARISON OF TUBES CONTAINING COVALENTLY BOUND IgG WITH TUBES CONTAINING ADSORBED IgG

| Experiment | Control Tubes (IgG Adsorbed) | Tubes with IgG Covalently Bound |
|---|---|---|
| Protein loss, based on counts/minute (Average of 6 tubes) | 22% | 11% |
| Functionality, Adsorbance with 400 pg/tube $T_4$ (Average of 6 tubes) | 0.209 | 0.276 |
| Functionality, Adsorbance with 4,800 pg/tube $T_4$ (Average of 6 tubes) | 0.092 | 0.105 |

EXAMPLE 4

Coating Porcelain and Adsorbing a Polypeptide Glycoprotein

Modified "Sandwich" Immunoassay

One third of the surface area of a Coors Porcelain Co. (600 Ninth St., Golden, Colo. 80401) porcelain plate (Stock No. 55105) was covered with masking tape, and the plate was heated to about 50° C. and immersed in a 3.1% suspension of the Dow Chemical XD-8931 polymer above (Lot AD 0906914.1). The plate was drained, air dried and cured at 141° C. Human chorionic gonadotropin (HCG) (Organon, West Orange, N.J., (Lot No. D-12899)) was dissolved in 0.9 ml of 0.1 M phosphate buffer pH 7.6. It was subsequently diluted to 0.33 mg/ml and 0.5 ml applied to some wells of the Coors plate for adsorption; other wells were left unadsorbed. The HCG solution was adsorbed onto the Coors plate for 24 hours at room temperature (about 25° C.), aspirated, rinsed twice with 0.1 M phosphate buffered saline containing bovine serum albumin, rinsed once with water and desiccated at room temperature.

Figure 3:
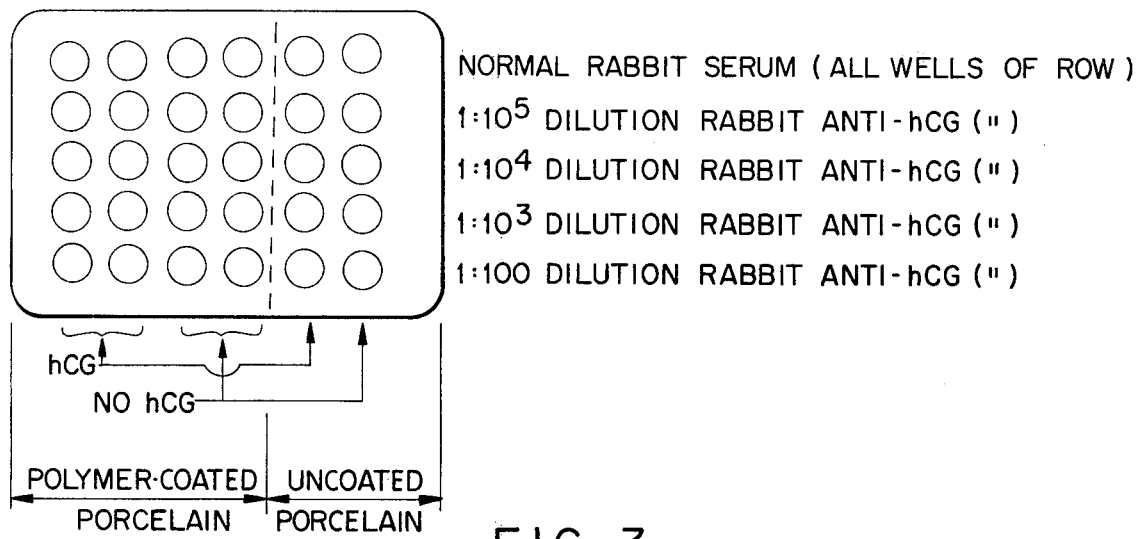
FIG. 3 displays from the vertical a porcelain plate having thirty (30) wells, and illustrates the presence (or absence) of HCG and the concentration of anti-HCG; the plate is used in Example 4, prior to testing.

Normal rabbit serum and serum from a rabbit hyperimmunized against HCG were each diluted in a solution containing 0.1 M phosphate buffer, pH 7.6, 0.2% bovine serum albumin and 0.9% saline. Dilutions of the specific anti-HCG serum from 1:100 to $1:10^5$ were prepared. 100 μl of each was incubated in the appropriate wells of the porcelain plate as indicated in FIG. 3.

Figure 4:
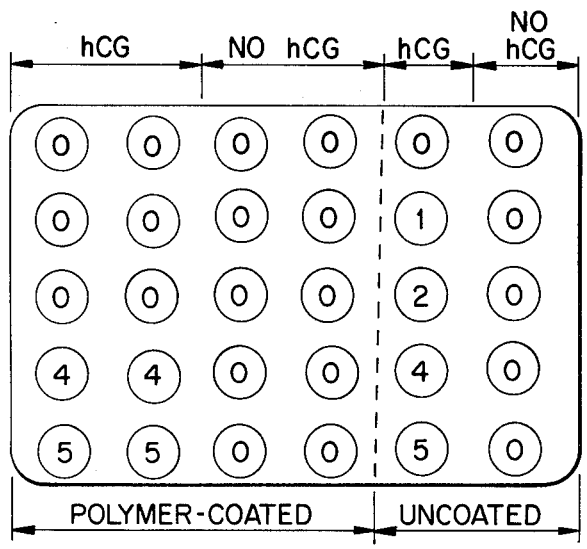
FIG. 4 shows the same porcelain plate as FIG. 3 after testing and the color of the solutions in the thirty (30) wells.

After about two hours of incubation at room temperature, all wells were aspirated and rinsed five times with a solution of (200 μl, 200 μl, 500 μl×3) 0.01% TRITON ® (Rohm and Haas) N-101 wetting agent in water. Then 0.3 ml of a preparation of peroxidase conjugated to specific goat antibody to rabbit IgG (Catalog No. 8838-15, Bionetics Inc., Kensington, MD., log CB013) (vial contents dissolved in 10 ml, ∼0.01 mg specific antibody per ml of reconstituted solution), incubated again for about one hour at room temperature and washed five times with 500 μl solution of TRITON ® wetting agent. Enzyme activity was detected by adding to each well 0.3 ml of a solution containing 35 mg o-phenylenediamine dihydrochloride substrate and 10 mg urea peroxide per 50 ml citrate-phosphate buffer as in Example 1. The color reaction was stopped and color fixed by 0.1 M citrate-0.1% $NaN_3$ solution after about three minutes and the color noted, as shown in FIG. 4.

EXAMPLE 5

Coating Stainless Steel and Adsorbing an Enzyme

Twelve stainless steel spatulas (VWR Scientific Co., Inc., Subsidiary of UniVar Corp., P.O. Box 3200, San Francisco, Calif. 94119, Cat. 57949-088) were cleaned with isopropanol, dried and heated to about 50° C. A solution of 24.4% by weight Dow Chemical XD-8931 polymer was likewise heated to about 50° C. Six warm spatulas were partially immersed (dipped) into the polymeric suspension, shaken to remove excess material, air-dried, and cured for one hour at about 110° C.

A solution of horseradish peroxidase, 7.5 mg/10 ml (Sigma Chemical Co. No. P-8375, type VI, 25,000 units/vial, E.C. 1.11.1.7., lot 59C-9760) was dissolved in $K_2CO_3$ buffer, pH 7.0 and aliquoted 1.0 ml/tube into 13 mm×100 mm glass tubes. The tips of three polymer-coated stainless steel spatulas and three uncoated stainless steel spatulas were then partially immersed in the enzyme solution and adsorbed for one hour at room temperature. The spatulas containing peroxidase were then rinsed forcefully with a stream of deionized water containing 0.01% TRITON ® N-101 solution. The tips of the spatulas and of control spatulas were immersed in peroxidase substrate as described in previous examples for a short time and color permitted to develop. Color was fixed as before, and the tubes read at 455 nm in a spectrophotometer. Table 4 gives the results of this coating experiment. Functional peroxidase activity was taken up by both the polymer-coated stainless steel and bare stainless steel. Control stainless steel, coated and uncoated, had no enzymatic activity.

TABLE 4

| Support (duplicates) | Absorbances Individual | Average |
|---|---|---|
| Water blank | 0.001, 0.002 | 0.002 |
| Uncoated stainless steel spatulas, with enzymes | 0.505, 0.508 | 0.507 |
| Coated stainless steel spatulas, without enzymes | 0.000, 0.002 | 0.001 |
| Coated stainless steel spatulas, with enzyme | 0.192, 0.195 | 0.194 |

EXAMPLE 6

Coating Nylon and Adsorbing Bacteria (*Escherichia coli*)

Twelve 2"×2"×0.031" squares of nylon were cut from a strip of "Nylon 101" (McMaster-Carr Co., 9601 South John, Los Angeles, Calif.), washed with detergent and water and soaked (degreased) in 70% isopropanol. A 10% suspension of Dow Chemical XD-8931 polymer was prepared and warmed to 50° C. The nylon squares were also warmed to about 50° C., and then they were immersed completely in the film-forming suspension. They were removed, drained, air-dried, and cured at about 133° C. for one hour. Before use, all coated or uncoated nylon squares were heat sterilized at about 133° C. for about one hour (in addition to curing times).

A cultured suspension of *Escherichia coli* was centrifuged and washed repeatedly to obtain a heavy opalescent suspension of *E. coli* in water. This suspension was poured into plastic weigh boats and coated or uncoated nylon squares immersed in the suspension for from about 20 seconds to about 3 minutes. Each square was sequentially rinsed in six baths of sterile water and then applied to sterile hard agar in petri dishes. Control plates were rinsed six times in sterile water and applied to agar plates without dipping in bacteria.

Table 5 shows the growth seen after an overnight culture of all squares on agar at about 37° C.

TABLE 5

| | Specimen | Culture Result |
|---|---|---|
| 1 | Culture dish control | No growth seen. |
| 3 | Uncoated nylon controls | No growth seen. |
| 3 | Coated nylon controls | No growth seen. |
| 3 | Uncoated nylon squares with adsorbed bacteria | Heavy growth of colonies at air-nylon interfaces. |
| 3 | Polymer-coated squares with adsorbed bacteria | Heavy growth of colonies at air-coating interfaces. |

EXAMPLE 7

The following Example is outside the scope of this invention and is relevant to the invention filed on even date, Ser. No. 170,304.

Coating Glass from Nonaqueous-Solvent-Based Polymer with Adsorption of Antibody 750 mg of a copolymer of styrene and allyl alcohol (molecular weight about 1150, 7.3–8% hydroxyl group content, Aldrich Chemical Company, 940 West St. Paul Ave., Milwaukee, Wis. 53233, No. 19,111-6) was dissolved in 1 ml of methylene chloride to make a solution of polymer. The polymer solution was pipetted into 13×100 mm glass tubes and then removed by aspiration. The tubes were air-dried to remove solvent and coated with anti-thyroxine antibodies as purified anti-thyroxine IgG as was done in Example 1. The tubes were rinsed with 0.1 M phosphate, pH 7.6, containing 0.9% saline. Then 100 μl radioiodinated thyroxine (about 65,000 dpm 125$_I$ per tube), and phosphate buffer containing saline and 0.2% added bovine serum albumin were added to bring the incubation volume to 1.0 ml. In some tubes, 10 ng unlabeled thyroxine was added as well. The tubes were incubated for about one hour at room temperature (25° C.), rinsed twice with 3 ml solution of 0.01% TRITON ® N-101 wetting agent (decanted), blotted and counted. The results of this experiment are given in Table 6. Functional antibody capable of binding radioiodinated thyroxine and of participating in displacement of the radioiodinated tag by unlabeled thyroxine is attached to the tube walls.

TABLE 6

| Tube Type | Disintegrations/Minute on Walls of tubes |
|---|---|
| Uncoated glass with antibody | 1,438 |
| Polymer-coated glass with antibody | 15,851 |
| Polymer-coated glass with antibody and 10 ng/tube unlabeled thyrozine added | 10,935 |

I claim:

1. Device for use in a bioprocess, comprising:
   (a) transparent glass solid support means insoluble in a solvent solution, selected from the group consisting of water and organic solvent solutions, which solid support means is coated with water-based synthetic polymeric film means; and
   (b) one or more functional biomaterials adsorbed or covalently bonded to said polymeric films.

2. Device of claim 1, wherein the solid support means is water-insoluble and water-insuspensible.

3. Device of claim 1 or claim 2, wherein the functional biomaterial is selected from the group consisting of an antigen, an antibody and a hapten, and the bioprocess is an immunoassay.

4. Process for manufacturing of a device for use in a bioprocess, comprising:
(a) providing a transparent glass solid support means insoluble in water or organic solvent solutions;
(b) coating said solid support means with water-based synthetic polymeric film means; and
(c) adsorbing or covalently bonding at least one functional biomaterial to said polymeric film means.

5. The process of claim 4, wherein the solid support means is water-insoluble and water-insuspensible.

6. The process of claim 4 or claim 5, wherein the functional biomaterial is selected from the group consisting of an antigen, an antibody and a hapten, and the bioprocess is an immunoassay.

7. Bioprocess using a device containing at least one functional biomaterial, the improvement wherein the device comprises:
(a) transparent glass solid support means insoluble in a solvent selected from the group consisting of water and organic solutions which solid support means is coated with water-solvent-based synthetic polymeric film means; and
(b) one or more functional biomaterials adsorbed or covalently bonded to said polymeric films.

8. The bioprocess of claim 7, wherein the solid support means is water-insoluble and water-insuspensible.

9. The bioprocess of claim 7 or claim 8, wherein the functional biomaterial is selected from the group consisting of an antigen, an antibody and a hapten, and the bioprocess is an immunoassay.

10. Process for manufacture of a device for use in a bioprocess, comprising:
(a) providing transparent glass solid support means insoluble in water or organic solvent solutions;
(b) heating a water-based, film-forming synthetic polymeric suspension from about 20° C. to about 100° C.;
(c) coating said solid support means with said heated aqueous-solvent polymeric suspension;
(d) drying the coated solid support means to remove any water to form a polymeric film on said solid support means;
(e) heating the solid support means having said film from about 100° C. to about 200° C. for a time sufficient to cure said film;
(f) cooling the solid support means having said cured film to a temperature suitable for applying one or more functional biomaterials to said cured film; and
(g) adsorbing or covalently bonding at least one functional biomaterial to said polymeric film means.

11. The process of claim 10, wherein the solid support means is heated in step (e) from about 1 minute to about 2 hours.

12. The process of claim 10, wherein the solid support means is cooled in step (f) to about room temperature.

13. The process of claim 10, wherein the solid support is water-insoluble and water-insuspensible.

14. The process of claim 10, wherein the functional biomaterial is selected from the group consisting of an antibody, an antibody and a hapten, and the bioprocess is an immunoassay.

15. The process of claim 10, wherein the solid support means consists essentially of a glass tube.

* * * * *